US011229719B2

United States Patent
Locke et al.

(10) Patent No.: US 11,229,719 B2
(45) Date of Patent: Jan. 25, 2022

(54) WOUND DRESSING LAYER FOR IMPROVED FLUID REMOVAL

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 273 days.

(21) Appl. No.: 16/473,169

(22) PCT Filed: Jan. 3, 2018

(86) PCT No.: PCT/US2018/012212
§ 371 (c)(1),
(2) Date: Jun. 24, 2019

(87) PCT Pub. No.: WO2018/129062
PCT Pub. Date: Jul. 12, 2018

(65) Prior Publication Data
US 2020/0085992 A1    Mar. 19, 2020

Related U.S. Application Data

(60) Provisional application No. 62/444,127, filed on Jan. 9, 2017.

(51) Int. Cl.
*A61M 35/00* (2006.01)
*A61L 15/42* (2006.01)
*A61F 13/00* (2006.01)
*A61L 15/26* (2006.01)

(52) U.S. Cl.
CPC ...... *A61L 15/425* (2013.01); *A61F 13/00068* (2013.01); *A61L 15/26* (2013.01)

(58) Field of Classification Search
CPC .............................................. A61F 2013/00634
See application file for complete search history.

(56) References Cited

U.S. PATENT DOCUMENTS

| | | |
|---|---|---|
| 1,355,846 A | 10/1920 | Rannells |
| 2,547,758 A | 4/1951 | Keeling |
| 2,632,443 A | 3/1953 | Lesher |

(Continued)

FOREIGN PATENT DOCUMENTS

| | | |
|---|---|---|
| AU | 550575 B2 | 3/1986 |
| AU | 745271 B2 | 3/2002 |

(Continued)

OTHER PUBLICATIONS

International Search Report and Written Opinion for Corresponding Application No. PCT/US2018/012212, dated Mar. 16, 2018.

(Continued)

*Primary Examiner* — Kim M Lewis (57) ABSTRACT

A wound dressing layer may include an open-cell foam. The foam may have a 50% compression force deflection of not more than about 4.8 kPa. The foam may also have a density of at least 24 kg/m³. The foam may exhibit a density increase of a factor of at least 12 at about −75 mmHg.

20 Claims, 1 Drawing Sheet

(56) References Cited

U.S. PATENT DOCUMENTS

| | | | |
|---|---|---|---|
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,268,224 A | 12/1993 | DesMarais et al. |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2007/0282029 A1* | 12/2007 | Hager ............... C08G 18/4072 521/172 |
| 2010/0055157 A1* | 3/2010 | Gunn ....................... A61L 15/18 424/447 |
| 2012/0107439 A1* | 5/2012 | Sharma .................. A61L 27/58 425/4 R |
| 2014/0163491 A1 | 6/2014 | Schuessler et al. |
| 2014/0271533 A1* | 9/2014 | Freyman .......... A61B 17/12118 424/78.38 |
| 2015/0080788 A1 | 3/2015 | Blott et al. |
| 2015/0320434 A1* | 11/2015 | Ingram ............ A61B 17/22004 606/131 |
| 2018/0235646 A1* | 8/2018 | Locke ..................... A61M 1/85 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| EP | 2959922 A1 | 12/2015 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |

(56) References Cited

FOREIGN PATENT DOCUMENTS

| | | |
|---|---|---|
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 9304092 A1 | 3/1993 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2012022485 A1 | 2/2012 |
| WO | 2013007093 A1 | 1/2013 |
| WO | 2013007973 A2 | 1/2013 |
| WO | 2015172111 A1 | 11/2015 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu A., et al; "Bacteriological and Cytological Assessment of Vacuum Therapy for Purulent Wounds" Vestnik Khirugi, Oct. 1988, pp. 48-52, and 8 page English translation thereof.

Davydov, Yu A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, p. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinoví?, V. ?ukí?, Ž. Maksimoví?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al.. Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

(56) References Cited

OTHER PUBLICATIONS

V.A.C. ® Therapy Clinical Guidelines: A Reference Source for Clinicians; Jul. 2007.
Chinese First Office Action for Corresponding Application No. 2018800094344, dated Mar. 25, 2021.

* cited by examiner

WOUND DRESSING LAYER FOR IMPROVED FLUID REMOVAL

RELATED APPLICATIONS

The present invention claims the benefit, under 35 USC § 119(e), of the filing of U.S. Provisional Patent Application Ser. No. 62/444,127, entitled "Wound Dressing Layer For Improved Fluid Removal," filed Jan. 9, 2017. This provisional application is incorporated herein by reference for all purposes.

TECHNICAL FIELD

The present technology relates to wound dressing layers for application to a wound, to wound dressings including such a wound dressing layer, to systems including such a wound dressing, and to methods related to the same.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, improvements to therapy systems, components, and processes may benefit healthcare providers and patients.

BRIEF SUMMARY

Systems, apparatuses (for example, a wound dressing layer), and methods for using the same, for example, in a negative-pressure therapy environment, are set forth in the appended claims. Illustrative embodiments are also provided to enable a person skilled in the art to make and use the claimed subject matter.

For example, disclosed herein are embodiments of a wound dressing layer. The wound dressing layer may comprise an open-cell foam. The foam may have a 50% compression force deflection of not more than about 4.8 kPa. Also, the foam also has a density of at least 24 kg/m³. The foam may exhibit a density increase of a factor of at least 12 at about −75 mmHg.

Also, disclosed herein are embodiments of a negative-pressure system for providing negative-pressure therapy to a tissue site. The system may comprise a wound dressing layer. The wound dressing layer may comprise an open-cell foam. The foam has a 50% compression force deflection of not more than about 4.8 kPa. Also, the foam may also have a density of at least 24 kg/m³. The foam may exhibit a density increase of a factor of at least 12 at about −75 mmHg. Further, the system may comprise a cover configured to be placed over the wound dressing layer. The cover may be sealed to tissue surrounding the tissue site to form a sealed space. Further still, the system may comprise a negative-pressure source configured to be fluidly coupled to the sealed space.

Also disclosed herein are embodiments of a method for providing negative-pressure therapy to a tissue site. The method may comprise positioning a wound dressing layer proximate to the tissue site. The wound dressing layer may comprise an open-cell foam. The foam may have a 50% compression force deflection of not more than about 4.8 kPa. Also, the foam may also have a density of at least 24 kg/m³. The foam may exhibit a density increase of a factor of at least 12 at about −75 mmHg. The method may also comprise placing a sealing member over the wound dressing layer and sealing the sealing member to tissue surrounding the tissue site to form a sealed space. The method may also comprise fluidly coupling a negative-pressure source to the sealed space. The method may also comprise operating the negative-pressure source to draw fluid from the tissue site through the wound dressing layer and generate a negative pressure in the sealed space.

Objectives, advantages, and a preferred mode of making and using the claimed subject matter may be understood best by reference to the accompanying drawing in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawing. In general, such relationships or orientation assume a frame of reference consistent with or relative to a patient in a position to receive treatment. However, as should be recognized by those skilled in the art, this frame of reference is merely a descriptive expedient rather than a strict prescription.

Disclosed herein are embodiments of a dressing for example, a wound dressing comprising a wound dressing layer for improved fluid removal, referred to herein as a dressing layer. Also, disclosed herein are embodiments of a dressing including such a dressing layer, and negative-pressure therapy systems including the same. Also disclosed herein are embodiments of methods related to the dressing layers, the dressings, and the negative-pressure therapy systems.

Figure 1:
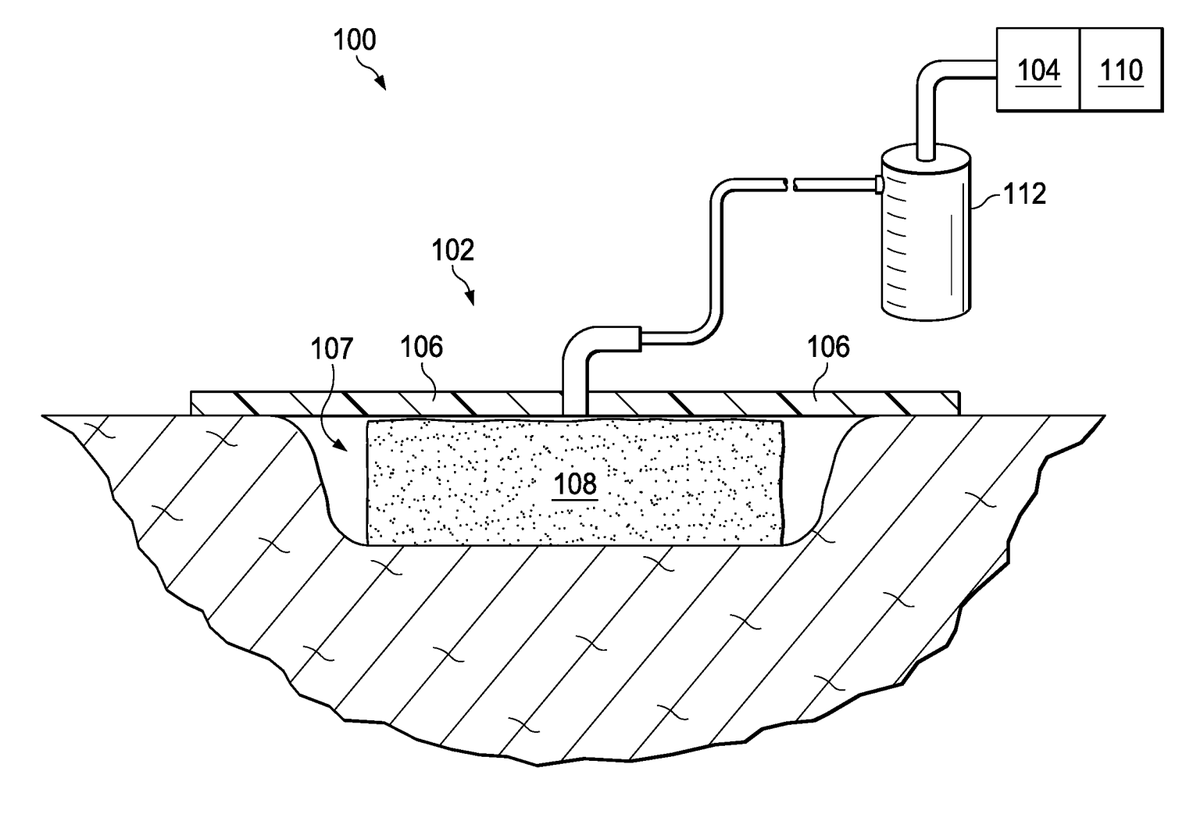
FIG. 1 is a simplified schematic of an example embodiment of a negative-pressure therapy system including a wound dressing layer in accordance with this specification.

Referring to FIG. 1, an embodiment of a negative-pressure therapy system 100 is shown in a simplified schematic. Generally, the negative-pressure therapy system 100 may be configured to provide negative pressure to a tissue site in accordance with the disclosure of this specification.

As used herein the term "tissue site" is intended to broadly refer to a wound, defect, or other treatment target located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue.

In various embodiments, the negative-pressure therapy system generally includes a negative-pressure supply, and may include or be configured to be coupled to a distribution component, such as a wound dressing. In general, a distribution component may refer to any complementary or ancillary component configured to be fluidly coupled to a negative-pressure supply in a fluid path between a negative-pressure supply and a tissue site. A distribution component may be detachable and, as well, may be disposable, reusable, or recyclable. For example, in the embodiment of FIG. 1, the negative-pressure therapy system 100 includes a wound dressing 102 that is illustrative of a distribution component fluidly coupled to a negative-pressure source 104.

As will be appreciated by the person of ordinary skill in the art upon viewing this disclosure, the fluid mechanics associated with using a negative-pressure source to reduce pressure in another component or location, such as within a sealed therapeutic environment, can be mathematically complex. However, the basic principles of fluid mechanics applicable to negative-pressure therapy are generally well-known to those skilled in the art. Herein, the process of reducing pressure may be described generally and illustratively herein as "delivering," "distributing," "providing," or "generating" negative pressure, for example.

In general, a fluid, such as wound fluid (for example, wound exudates and other fluids), flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

As used herein, "negative pressure" is generally intended to refer to a pressure less than a local ambient pressure, such as the ambient pressure in a local environment external to a sealed therapeutic environment provided by the wound dressing 102. In many cases, the local ambient pressure may also be the atmospheric pressure proximate to or about a tissue site. Alternatively, the pressure may be less than a hydrostatic pressure associated with the tissue at the tissue site. Unless otherwise indicated, values of pressure stated herein are gauge pressures. Similarly, references to increases in negative pressure typically refer to a decrease in absolute pressure (e.g., a "more negative" pressure), while decreases in negative pressure typically refer to an increase in absolute pressure (e.g., a "less negative" pressure or a "more positive" pressure). While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

In various embodiments, a negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source may be combined with one or more other components into a therapy unit. A negative-pressure supply may also have one or more supply ports configured to facilitate coupling and de-coupling of the negative-pressure supply to one or more distribution components.

In the embodiment of FIG. 1, the negative-pressure therapy system 100 includes a controller 110. The controller 110 may also be coupled to the negative-pressure source 104. The controller 110 may generally be configured to control one or more operational parameters associated with the negative-pressure therapy system. While in some embodiments a negative-pressure therapy system like the negative-pressure therapy system 100 of FIG. 1 may include one or more sensors, for example, to measure operating parameters and provide feedback signals indicative of those operating parameters to a controller like the controller 110, in other embodiments, such sensors need not be included, as will be disclosed herein. For example, in the embodiment of FIG. 1, the negative-pressure therapy system 100 does not include any pressure sensor coupled a distribution component (such as the wound dressing 102) and to the controller 110 and configured to provide feedback to the controller 110, such as the pressure within the distribution component. In such an embodiment, the controller 110 may be characterized as an "open loop" controller. A controller, such as the controller 110, may be a microprocessor or computer programmed to operate one or more components of the negative-pressure therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the negative-pressure therapy system 100. Operating parameters may include the power applied to the negative-pressure source 104, the pressure generated by the negative-pressure source 104, or the pressure distributed to the dressing layer 108, for example. The controller 110 may also be configured to receive one or more input signals, such as an input signal from a user interface.

In some embodiments, the negative-pressure source 104 may be operatively coupled to the wound dressing 102 via a dressing interface. In the embodiment of FIG. 1, the wound dressing 102 is coupled to the negative-pressure source 104 such that the wound dressing 102 receives negative pressure from the negative-pressure source 104. In some embodiments, the negative-pressure therapy system 100 may include a fluid container, such as a container 112, fluidly coupled to the wound dressing 102 and to the negative-pressure source 104. The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

In various embodiments, components may be fluidly coupled to each other to provide a path for transferring fluids (i.e., liquid and/or gas) between the components. For example, components may be fluidly coupled through a fluid conductor, such as a tube. As used herein, the term "tube" is intended to broadly include a tube, pipe, hose, conduit, or other structure with one or more lumina adapted to convey a fluid between two ends thereof. Typically, a tube is an elongated, cylindrical structure with some flexibility, but the geometry and rigidity may vary. In some embodiments, two or more components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the wound dressing 102 to the container 112 in some embodiments. In general, components of the negative-pressure therapy system 100 may be coupled directly or indirectly. For example, the negative-pressure source 104 may be directly coupled to the controller 110, and may be indirectly coupled to the wound dressing 102, for example, through the container 112.

Wound Dressing

Often, in the context of negative-pressure therapy, negative pressure may be applied to a tissue site (e.g., a wound) via materials and devices generally characterized as "wound dressings." Generally, in addition to providing for the application of negative pressure to a tissue site, wound dressings may control bleeding, ease pain, assist in debriding the wound, protect wound tissue from infection, modulate protease activity, or otherwise promote healing and protect the wound from further damage. In some embodiments, a wound dressing may include a cover, one or more layers configured to interface with the tissue site, or combinations thereof. For example, in the embodiment of FIG. 1, the wound dressing 102 includes a dressing layer 108 and a cover 106.

Wound Dressing—Cover

In various embodiments, the cover 106 may generally be configured to provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. In some embodiments, the cover 106 may have a high moisture-vapor transmission rate (MVTR), for example, for some applications. In such an embodiment, the MVTR may be at least 300 $g/m^2$ per twenty-four hours. In some embodiments, the cover 106 may be formed from a suitable polymer. For example, the cover 106 may comprise a polymer drape, such as a polyurethane film, that may be permeable to water vapor but generally impermeable to liquid. In such embodiments, the drape may have a thickness in the range of about from 25 to about 50 microns. In embodiments where the cover comprises a permeable material, the cover 106 may have a permeability sufficiently low that a desired negative pressure may be maintained.

In some embodiments, the cover 106 may be configured to be attached to an attachment surface, such as undamaged epidermis, a gasket, or another cover, for example, via an attachment device. For example, in the embodiment of FIG. 1, the cover is shown attached to epidermis so as to form a sealed space 107. In such an embodiment, the attachment device may take any suitable form. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments, for example, to improve the seal and reduce leaks. Other example embodiments of an attachment device may include a double-sided tape, a paste, a hydrocolloid, a hydrogel, a silicone gel, or an organogel.

Wound Dressing—Dressing Layer

In various embodiments, the dressing layer 108 may be generally configured to distribute negative pressure, for example, so as to collect fluid. For example, in some embodiments, the dressing layer 108 may comprise or be configured as a manifold. A "manifold" in this context generally includes any composition or structure providing a plurality of pathways configured to collect or distribute fluid across a tissue site under pressure. For example, a manifold may be configured to receive negative pressure from a negative-pressure source and to distribute negative pressure through multiple apertures (pores), which may have the effect of collecting fluid and drawing the fluid toward the negative-pressure source. More particularly, in the embodiment of FIG. 1, the dressing layer 108 is configured to receive negative pressure from the negative-pressure source 104 and to distribute the negative pressure through the dressing layer 108, for example, which may have the effect of collecting fluid from the sealed space 107, for example, by drawing fluid from the tissue site through the dressing layer 108. In additional or alternative embodiments, the fluid path(s) may be reversed or a secondary fluid path may be provided to facilitate movement of fluid across a tissue site.

In some illustrative embodiments, the fluid pathways of a manifold may be interconnected to improve distribution or collection of fluids. In some embodiments, a manifold may be a porous foam material having a plurality of interconnected cells or pores. For example, cellular foams, open-cell foams, and reticulated foams generally include pores, edges, and/or walls adapted to form interconnected fluid pathways such as, channels. In various embodiments, foam-forming materials may be formed into a foam, such as by curing, so as to include various apertures and fluid pathways. In some embodiments, a manifold may additionally or alternatively comprise projections that form interconnected fluid pathways. For example, a manifold may be molded to provide surface projections that define interconnected fluid pathways.

In the embodiment of FIG. 1, the dressing layer 108 comprises or consists essentially of a foam, for example, an open-cell foam, a reticulated foam, or combinations thereof. In such an embodiment, the average pore size of such a foam may vary according to needs of a prescribed therapy. For example, in some embodiments, the dressing layer 108 may be a foam having pore sizes in a range of 400-600 microns. The tensile strength of the dressing layer 108 may also vary according to needs of a prescribed therapy.

In various embodiments, the dressing layer 108 may be generally configured to be in contact with the tissue site. For example, the dressing layer 108 may be in contact with a portion of the tissue site, substantially all of the tissue site, or the tissue site in its entirety. If the tissue site is a wound, for example, the dressing layer 108 may partially or completely fill the wound, or may be placed over (e.g., superior to) the wound. In various embodiments, the dressing layer 108 may take many forms, and may have many sizes, shapes, or thicknesses depending on a variety of factors, such as the type of treatment being implemented or the nature and size of a tissue site. For example, the size and shape of the dressing layer 108 may be adapted to the contours of deep and irregular shaped tissue sites and/or may be configured so as to be adaptable to a given shape or contour. Moreover, in some embodiments, any or all of the surfaces of the dressing layer 108 may comprise projections or an uneven, course, or jagged profile that can, for example, induce strains and stresses on a tissue site, for example, which may be effective to promote granulation at the tissue site.

Foam materials may be characterized by an elastic modulus, which may also be referred to as a foam modulus. Generally, the elastic modulus of a material, such as the dressing layer 108, may be a measure of the resistance of the material to elastic deformation under a load. The elastic modulus of a material may be defined as the slope of a stress-strain curve in the elastic deformation region of the curve. The elastic deformation region of a stress-strain curve represents that portion of the curve where deformation of a material due to an applied load is elastic, that is, not permanent. If the load is removed, the material may return to its pre-loaded state. Generally, relatively "stiff" or "stiffer" materials may exhibit a relatively high elastic modulus and, conversely, relatively more compliant materials may exhibit a relatively low elastic modulus. Generally, a reference to the elastic modulus of a material refers to a material under tension.

Similarly, for some materials under compression, the elastic modulus can be compared between materials by comparing the compression force deflection of the respective materials. For instance, the compression force deflection may be determined experimentally by compressing a sample of a material until the sample is reduced to about 25% of its uncompressed size. Alternatively, the compression force deflection may also be measured by compressing a sample of a material to about 50% of its uncompressed size. Generally, the load applied to the sample to reach the compressed state of the sample is then divided by the area of the sample over which the load is applied to yield the compression force deflection. The compression force deflection of a foam material can, inter alia, be a function of compression level, polymer stiffness, cell structure, foam density, and cell pore size.

In some embodiments, the dressing layer 108 may be characterized as a relatively soft material. For example, in some embodiments, the dressing layer 108 may have a 50% compression force deflection of not more than about 4.8 kPa, for example, from about 0.5 kPa to about 4.8 kPa or, in a more particular embodiment, from about 2.0 kPa to about 4.8 kPa. That is, the dressing layer 108 may exhibit compression of about 50% of its uncompressed size if a load of not more than about 4.8 kPa is applied to the dressing layer 108. Additionally, compression force deflection can represent the tendency of a foam to return to its uncompressed state if a load is applied to compress the foam. For example, a dressing layer 108 comprising or consisting essentially of foam and characterized having a 50% compression force deflection of about 4.8 kPa may exert about 4.8 kPa in reaction to 50% compression.

Further, foam materials, for example, the dressing layer 108, may be characterized with respect to density. In some embodiments, the dressing layer 108 may be characterized as a relatively dense material. For example, in various embodiments, the dressing layer 108 may have a density of from about 24 kg/m$^3$ to about 125 kg/m$^3$ or, in a more particular embodiment, from about 24 kg/m$^3$ to about 72 kg/m$^3$.

Also, foam materials may be characterized as having a particular free volume. In some embodiments, the dressing layer 108 may have a free volume resulting from, for example, pores, channels, and other void-spaces within a foam material. For example, in various embodiments, a foam dressing layer 108 may be characterized as exhibiting a suitable free volume, which may be calculated as the mass of the foam divided by the density of the foam.

Foam materials may also be characterized by a particular porosity and pore size. The number of pores and the average pore size of the foam may vary according to needs of a prescribed therapy. For example, in various embodiments, a foam dressing layer 108 may be characterized as exhibiting a porosity of from about 20 pores per inch to about 120 pores per inch. Additionally, in various embodiments, a foam dressing layer 108 may have an average pore size in a range of from about 400 to about 600 microns.

Foam materials may also be characterized with respect to changes in density upon the application of a compressive force. For example, as noted herein, a foam may exhibit a particular compression force deflection (e.g., compression resultant from the application of a force to the foam). More particularly, a foam embodiment of the dressing layer 108 may be characterized as exhibiting a change in density responsive to the application of a particular negative pressure, for example, a negative pressure effective to cause the ambient, atmospheric pressure to exert a compressing force with respect to a foam piece within a sealed space to which the negative pressure is applied The density change may be observed by placing a foam a onto a flat surface, such as a sheet of plastic or metal, placing a flexible drape over the foam, connecting the interior space to a particular negative pressure, and measuring the thickness of foam at various applied negative pressures. For example, in some embodiments, the dressing layer 108 may be characterized as exhibiting a density increase of a factor of at least 5 (that is, the dressing layer 108 becomes five times more dense) at about −25 mmHg, a density increase of a factor of at least 9 at about −50 mmHg, a density increase of a factor of at least 12 at about −75 mmHg, a density increase of a factor of at least 14 at about −100 mmHg, a density increase of a factor of at least 16 at about −125 mmHg, or combinations thereof. For example, in some embodiments, the dressing layer 108 may be characterized as exhibiting a density increase of a factor of at least 5 at about −25 mmHg, a density increase of a factor of at least 9 at about −50 mmHg, a density increase of a factor of at least 12 at about −75 mmHg, a density increase of a factor of at least 14 at about −100 mmHg, and a density increase of a factor of at least 16 at about −125 mmHg.

In some embodiments, the dressing layer 108 may be hydrophobic. For example, the dressing layer 108 may be characterized as a hydrophobic, open-cell foam. Not intending to be bound by theory, in such an embodiment, the hydrophobic characteristics may prevent the foam from directly absorbing fluid, such as wound exudate (e.g., from the tissue site), but may allow the fluid to pass, for example, through the internal structure. For example, in some embodiments, the foam may be a hydrophobic, open-cell polyurethane foam, a silicone foam, a polyether block amide foam, such as PEBAX®, an acrylic foam, a polyvinyl chloride (PVC) foam, a polyolefin foam, a polyester foam, a polyamide foam, a thermoplastic elastomer (TPE) foam such as a thermoplastic vulcanizate (TPV) foam, and other cross-linking elastomeric foam such as foams formed from styrene-butadiene rubber (SBR) and ethylene propylene diene monomer (EPDM) rubber.

In an alternative embodiment, the dressing layer 108 may be hydrophilic. Not intending to be bound by theory, in such an embodiment, the dressing layer 108 may be effective to wick fluid (e.g., away from the tissue site), for example, while also continuing to distribute negative pressure to the tissue site. Not intending to be bound by theory, in such an embodiment, the wicking properties of the dressing layer 108 may draw fluid away from the tissue site by capillary flow or other wicking mechanisms. An example of a hydrophilic foam may include a polyvinyl alcohol or polyether, open-cell foam. Other foams that may exhibit hydrophilic characteristics include hydrophobic foams that have been treated or coated to provide hydrophilicity. In one non-limiting example, the dressing layer 108 may be a treated open-cell polyurethane foam.

In various embodiments, the dressing layer 108 may be freeze dried, such as through lyophilization.

Methods

In operation, for example, in the context of a negative-pressure therapy, the dressing layer 108 may be placed within, over, on, or otherwise proximate to a tissue site, for example, a wound. The cover 106 may be placed over the dressing layer 108 and the cover 106 sealed to an attachment surface near the tissue site. For example, the cover 106 may be sealed to undamaged epidermis peripheral to a tissue site. Thus, the wound dressing 102, for example, the dressing layer 108 and the cover 106, can provide a sealed therapeutic environment, for example, a sealed space like sealed space 107, proximate to a tissue site, substantially isolated from the external environment. The negative-pressure source 104 may be used to reduce the pressure in such sealed therapeutic environment. For example, negative pressure applied across the tissue site, for example, via the dressing layer 108 can induce macrostrain and microstrain in the tissue site, as well as remove exudates and other fluids from the tissue site, which can be collected in container 112.

Advantages

The dressing layer, wound dressings including such a layer, and negative-pressure therapy systems disclosed herein may provide significant advantages, for example, when used in a negative-pressure therapy, as also disclosed herein.

In some embodiments, the disclosed dressing layers, wound dressings, and systems may be advantageously employed in the context of negative-pressure therapy, for example, to improve removal of wound fluid, such as wound exudate, for example, via the application of negative pressure. For example, a dressing layer of the type disclosed herein, for example, a foam dressing layer characterized as a relatively soft material, characterized as relatively more dense, and/or characterized as exhibiting a relatively high density increase at a particular negative pressure, may improve the quantity of fluid removed from a wound, the efficiency with which fluid is removed, or both. For example, and not intending to be bound by theory, fluid removal may be dependent upon the free volume within the foam and the compressibility of the foam. For example, generally, a foam having a relatively higher density and characterized as relatively softer, for example, having a relatively higher compression force deflection and/or characterized as exhibiting a relatively high density increase, will have a lesser free volume when compressed and, as such, will be more able to expel fluid. Referring to Table 1, below, the results of testing with regard to several foams varying as to density and/or pore size are shown:

|  | Sample 1 (Granufoam) | Sample 2 (45MC F3) | Sample 3 (45MA F3) | Sample 4 (45MA F5) |
| --- | --- | --- | --- | --- |
| Density (kg/m$^3$) | 4.8 | 15 | 15 | 20 |
| Pore Size (ppi) | 400-600μ | 120-200μ | 120-200μ | 80-130μ |
| Saline Collected | 70 ml | 60 ml | 60 ml | 55 ml |
| Wet Dressing Weight | 67.34 g | 83.64 g | 66.87 g | 70.57 g |
| Fluid in Dressing (g) | 5.84 g | 15.48 g | 16.06 g | 21.03 g |
| Fluid in Dressing (mL) | 5.89 ml | 15.60 ml | 16.19 ml | 21.20 ml |

As shown in Table 1, the lowest-density foam yielded the highest quantity of fluid removal. The two foams having a density of 15 kg/m$^3$ yielded very similar quantities of fluid removal; these foams yielded less fluid removal than the lowest-density foam, but more than the highest-density foam. The highest-density foam yielded the lowest quantity of fluid removal. Again not intending to be bound by theory, the above-testing generally demonstrates that lower foam densities tend to yield improved fluid removal, potentially, because of the corresponding stiffness of the more dense foams. More particularly, a more stiff foam may tend to oppose compression, for example, from the application of negative pressure, thereby allowing more fluid to remain in its pores. Also, a relatively low-density foam may have a relatively high free volume in which fluid can accumulate. Finally, a relatively high-density, low stiffness foam may tend to expel more fluid than a comparable foam with the same density but relatively higher stiffness, for example, in that the relatively stiffer foam is less able to be compress under a compressive force.

Thus, the dressing layers, the wound dressings including such a layer, and the negative-pressure therapy systems disclosed herein may allow for the modulation of fluid removal for example, from a tissue site, such as a wound, even when utilizing a system that does not provide feedback, such negative-pressure feedback, to the negative-pressure source and/or controller. As such, the disclosed dressing layers, the wound dressings including such a layer, and the negative-pressure therapy systems may allow for improved fluid removal, for example, such that an open-loop feedback system may be capable of achieving similar fluid removal to a closed-loop system having feedback but employing a conventional wound dressing layer. As used herein, an "open-loop system," which may also be referred to as a non-feedback system, may refer to a system in which an output from the system has no influence or effect on the control action of an input signal. For example, in an open-loop control system the output may not be "fed back" for purposes of altering the input. Also, as used herein, a "closed loop system," which may also be referred to as a feedback system, may refer to a system having one or more feedback loops between an output and an input. For example, in a closed-loop system some portion of the output may be returned "back" so as to alter the input.

The term "about," as used herein, is intended to refer to deviations in a numerical quantity that may result from various circumstances, for example, through measuring or handling procedures in the real world; through inadvertent error in such procedures; through differences in the manufacture, source, or purity of compositions or reagents; from computational or rounding procedures; and the like. Typically, the term "about" refers to deviations that are greater or lesser than a stated value or range of values by $\frac{1}{10}$ of the stated value(s), e.g., ±10%. For instance, a concentration value of "about 30%" refers to a concentration between 27% and 33%. Each value or range of values preceded by the term "about" is also intended to encompass the embodiment of the stated absolute value or range of values. Whether or not modified by the term "about," quantitative values recited in the claims include equivalents to the recited values, for example, deviations from the numerical quantity, but would be recognized as equivalent by a person skilled in the art.

The appended claims set forth novel and inventive aspects of the subject matter disclosed and described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A negative-pressure system for providing negative-pressure therapy to a tissue site, the system comprising:
    a wound dressing layer comprising an open-cell foam having a 50% compression force deflection of not more than about 4.8 kPa, a density of at least 24 kg/m$^3$, and exhibiting a density increase of a factor of at least 12 at about −75 mmHg; and
    a cover configured to be placed over the wound dressing layer and attached to tissue surrounding the tissue site; and
    a negative-pressure source configured to be fluidly coupled to the wound dressing layer.

2. The negative-pressure system of claim 1, having a 50% compression force deflection of not more than about 4.5 kPa.

3. The negative-pressure system of claim 1, having a 50% compression force deflection of not more than about 4.0 kPa.

4. The negative-pressure system of claim 1, having a 50% compression force deflection of not more than about 3.5 kPa.

5. The negative-pressure system of claim 1, having a 50% compression force deflection of not more than about 3.0 kPa.

6. The negative-pressure system of claim 1, having a density of at least 28 kg/m$^3$.

7. The negative-pressure system of claim 1, having a density of at least 32 kg/m$^3$.

8. The negative-pressure system of claim 1, having a density of at least 36 kg/m$^3$.

9. The negative-pressure system of claim 1, having a density of at least 40 kg/m$^3$.

10. The negative-pressure system of claim 1, exhibiting a density increase of a factor of at least 5 at about −25 mmHg.

11. The negative-pressure system of claim 1, exhibiting a density increase of a factor of at least 9 at about −50 mmHg.

12. The negative-pressure system of claim 1, exhibiting a density increase of a factor of at least 14 at about −100 mmHg.

13. The negative-pressure system of claim 1, exhibiting a density increase of a factor of at least 16 at about −125 mmHg.

14. The negative-pressure system of claim 1, wherein the open-cell foam is hydrophobic.

15. The negative-pressure system of claim 1, wherein the open-cell foam is formed from polyurethane.

16. The negative-pressure system of claim 1, wherein the negative-pressure source is an open loop negative-pressure source.

17. The negative-pressure system of claim 1, wherein the negative-pressure source is not configured to be controlled in response to a signal from a pressure sensor associated with a sealed space between the cover and the tissue site.

18. A method for providing negative-pressure therapy to a tissue site, the method comprising:
    positioning a wound dressing layer comprising an open-cell foam having a 50% compression force deflection of not more than about 4.8 kPa, a density of at least 24 kg/m$^3$, and exhibiting a density increase of a factor of at least 12 at about −75 mmHg proximate to the tissue site;
    placing a sealing member over the wound dressing layer and sealing the sealing member to tissue surrounding the tissue site to form a sealed space;
    fluidly coupling a negative-pressure source to the sealed space; and
    operating the negative-pressure source to draw fluid from the tissue site through the wound dressing layer and generate a negative-pressure in the sealed space.

19. The method of claim 18, wherein the negative-pressure system source does not receive feedback from a pressure sensor associated with the sealed space.

20. The method of claim 18, wherein the negative-pressure source is an open loop negative-pressure source.

* * * * *

UNITED STATES PATENT AND TRADEMARK OFFICE
CERTIFICATE OF CORRECTION

PATENT NO. : 11,229,719 B2
APPLICATION NO. : 16/473169
DATED : January 25, 2022
INVENTOR(S) : Christopher Brian Locke

Page 1 of 1

It is certified that error appears in the above-identified patent and that said Letters Patent is hereby corrected as shown below:

In the Claims

Column 12
Lines 50-51, In Claim 19, after "negative-pressure" delete "system".

Signed and Sealed this
Ninth Day of April, 2024

Katherine Kelly Vidal
*Director of the United States Patent and Trademark Office*